United States Patent
Betsinger et al.

(10) Patent No.: US 9,535,024 B2
(45) Date of Patent: Jan. 3, 2017

(54) SENSE AND HOLD CIRCUIT FOR HOSE ASSEMBLY

(71) Applicant: Eaton Corporation, Cleveland, OH (US)

(72) Inventors: James Dean Betsinger, Waterville, OH (US); Nicholas Adam Burtyk, Minnetonka, MN (US)

(73) Assignee: Eaton Corporation, Cleveland, OH (US)

( * ) Notice: Subject to any disclaimer, the term of this patent is extended or adjusted under 35 U.S.C. 154(b) by 408 days.

(21) Appl. No.: 14/026,091

(22) Filed: Sep. 13, 2013

(65) Prior Publication Data

US 2014/0076449 A1     Mar. 20, 2014

Related U.S. Application Data

(60) Provisional application No. 61/701,325, filed on Sep. 14, 2012, provisional application No. 61/701,344, filed on Sep. 14, 2012.

(51) Int. Cl.
    *G01R 31/08*     (2006.01)
    *G01R 27/08*     (2006.01)
    (Continued)

(52) U.S. Cl.
    CPC .............. *G01N 27/045* (2013.01); *F16L 11/00* (2013.01); *G01M 3/18* (2013.01); *G01M 5/0025* (2013.01);
    (Continued)

(58) Field of Classification Search
    CPC ...... G01R 27/02; G01N 27/045; G01N 27/02; F16L 2201/30; F16L 11/00
    (Continued)

(56) References Cited

U.S. PATENT DOCUMENTS

| 2,291,070 A | 7/1942 | Bruno |
| 2,436,949 A | 3/1948 | Anderson |

(Continued)

FOREIGN PATENT DOCUMENTS

| DE | 31 40 804 A1 | 4/1983 |
| DE | 40 30 788 A1 | 8/1991 |

(Continued)

OTHER PUBLICATIONS

International Search Report and Written Opinion for PCT/US2013/059473 mailed Jul. 18, 2014.

(Continued)

*Primary Examiner* — Amy He
(74) *Attorney, Agent, or Firm* — Merchant & Gould P.C.

(57) ABSTRACT

A monitoring circuit for detecting degradation of a hose assembly a hose assembly and a hose assembly incorporating such a monitoring circuit are disclosed. The monitoring circuit includes a voltage source connected to a first connection location of a hose assembly. A capacitor is electrically connected between the second connection location connected to the second conductive layer of a hose assembly and a ground. The capacitor is selected such that a change in resistance of the hose assembly changes a voltage carried by the capacitor. The monitoring circuit includes a voltage sampling circuit configured to periodically detect a voltage at the capacitor. Upon detecting a change in the voltage above a predetermined threshold, the voltage sampling circuit generates an alarm indicative of potential failure.

23 Claims, 8 Drawing Sheets

(51) Int. Cl.
*G01N 27/04* (2006.01)
*F16L 11/00* (2006.01)
*G08B 21/18* (2006.01)
*G01R 27/02* (2006.01)
*G01M 3/18* (2006.01)
*G01M 5/00* (2006.01)

(52) U.S. Cl.
CPC .......... *G01M 5/0033* (2013.01); *G01M 5/0083* (2013.01); *G01R 27/02* (2013.01); *G08B 21/182* (2013.01); *F16L 2201/30* (2013.01)

(58) Field of Classification Search
USPC ........................................ 324/522, 525, 713
See application file for complete search history.

(56) References Cited

U.S. PATENT DOCUMENTS

| | | |
|---|---|---|
| 4,029,889 A | 6/1977 | Mizuochi |
| 4,229,613 A | 10/1980 | Braun |
| 4,446,892 A | 5/1984 | Maxwell |
| 5,267,670 A | 12/1993 | Foster |
| 5,343,738 A | 9/1994 | Skaggs |
| 5,387,899 A | 2/1995 | DiLauro et al. |
| 5,442,810 A | 8/1995 | Jenquin |
| 5,551,484 A | 9/1996 | Charboneau |
| 5,634,497 A | 6/1997 | Neto |
| 5,671,689 A | 9/1997 | Clapp et al. |
| 5,969,618 A | 10/1999 | Redmond |
| 5,992,218 A | 11/1999 | Tryba et al. |
| 6,384,611 B1 | 5/2002 | Wallace et al. |
| 6,386,237 B1 | 5/2002 | Chevalier et al. |
| 6,498,991 B1 | 12/2002 | Phelan et al. |
| 6,735,705 B1 | 5/2004 | Egbert et al. |
| 6,958,615 B2 | 10/2005 | Poulbot et al. |
| 7,555,936 B2 | 7/2009 | Deckard |
| 8,087,430 B1 | 1/2012 | Betz et al. |
| 8,183,872 B2 | 5/2012 | Stark |
| 8,217,669 B1 | 7/2012 | Watkins, Jr. |
| 8,515,687 B2 | 8/2013 | Pereira et al. |
| 8,829,929 B1 | 9/2014 | Watkins, Jr. |
| 8,997,792 B2 | 4/2015 | Betsinger et al. |
| 2001/0018845 A1 | 9/2001 | Roberts |
| 2002/0154029 A1 | 10/2002 | Watters et al. |
| 2003/0164048 A1 | 9/2003 | Shkel |
| 2004/0065377 A1 | 4/2004 | Whiteley |
| 2005/0253821 A1 | 11/2005 | Roeder |
| 2006/0226701 A1 | 10/2006 | Gatz et al. |
| 2007/0051166 A1 | 3/2007 | Baker et al. |
| 2007/0131035 A1 | 6/2007 | Krutz et al. |
| 2008/0036617 A1 | 2/2008 | Arms et al. |
| 2010/0174495 A1 | 7/2010 | Pereira et al. |
| 2010/0308575 A1 | 12/2010 | Rodenburg |
| 2011/0152024 A1 | 6/2011 | Kuehl |
| 2011/0226302 A1 | 9/2011 | Farmer et al. |
| 2011/0281488 A1 | 11/2011 | Li |
| 2012/0136592 A1 | 5/2012 | Pereira et al. |
| 2012/0204923 A1 | 8/2012 | Ortiz et al. |
| 2012/0278018 A1 | 11/2012 | Hastreiter |
| 2013/0134992 A1 | 5/2013 | Zhu et al. |
| 2014/0238109 A1 | 8/2014 | Wells et al. |
| 2014/0265561 A1 | 9/2014 | Beining |
| 2015/0177172 A1 | 6/2015 | Upasani et al. |
| 2015/0240972 A1 | 8/2015 | Betsinger |
| 2015/0300538 A1 | 10/2015 | Al-Atat et al. |

FOREIGN PATENT DOCUMENTS

| | | |
|---|---|---|
| EP | 1 126 205 A1 | 8/2001 |
| EP | 1 722 217 A1 | 11/2006 |
| EP | 2 261 546 A1 | 12/2010 |
| GB | 1 574 749 | 9/1980 |
| JP | 2011027216 | 2/2011 |
| WO | WO 03/079749 A2 | 10/2003 |
| WO | WO 2008/001238 A2 | 1/2008 |
| WO | WO 2008/059226 A2 | 5/2008 |
| WO | 2011/143384 A1 | 11/2011 |
| WO | WO 2012/012482 A1 | 1/2012 |
| WO | WO 2012/071424 A2 | 5/2012 |
| WO | WO 2012/149161 A1 | 11/2012 |

OTHER PUBLICATIONS

Invitation to Pay Additional Fees with Partial International Search for PCT/US2013/059473 mailed Feb. 28, 2014.
International Search Report and Written Opinion for Application No. PCT/US2011/061865 mailed May 21, 2012.
International Search Report and Written Opinion for Application No. PCT/US2012/035216 mailed Jul. 16, 2012.
International Search Report and Written Opinion for Application No. PCT/US2014/017590 mailed Jun. 3, 2014.
International Search Report for Application No. PCT/IN2012/000296 mailed Nov. 27, 2012.
International Search Report for Application No. PCT/US2013/030966 mailed Aug. 1, 2013.
Invitation to Pay Additional Fees with Partial International Search for Application No. PCT/US2013/048660 mailed Mar. 24, 2014.
International Search Report and Written Opinion for Application No. PCT/US2013/048660 mailed Sep. 8, 2014.
International Search Report for Application No. PCT/US2013/059465 mailed Dec. 3, 2013.
International Search Report and Written Opinion for Application No. PCT/US2014/029286 mailed Jun. 18, 2014.
Holland, Z. et al., "Layered Polymer Whole Structure Health Monitoring Using Capacitance Sensing", *IEEE/ASME International Conference on Advanced Intelligent Mechatronics*, Montreal, Canada, Jul. 6-9, 2010, pp. 943-946.
Radtke et al., Design of Power-Transmitting Hydraulic Hose with Integrated Controller Area Network and Life-Sensing Capability, 2005 Agricultural Equipment Technology Conference, Feb. 15, 2005.
Guo, Z. et al., "GRE: Graded Residual Energy Based Lifetime Prolonging Algorithm for Pipeline Monitoring Sensor", *9th International Conference on Parallel and Distributed Computing Applications and Technologies*, 203-210 (2008).
Mohamed, M. et al., "Power Harvesting for Smart Sensor Networks in Monitoring Water Distribution System", *International Conference on Networking, Sensing and Control*, 393-398 (2011).
Ok, C. et al., "Optimal Transmission Power in Self-sustainable Sensor Networks for Pipeline Monitoring", *IEEE International Conference on Automation Science and Engineering*, 591-596 (2007).
European Search Report for Application No. 12875245.8 mailed Dec. 15, 2015.
Agilent 4263B LCR Meter 100 Hz to 100 kHz (Technical Overview), printed on Apr. 24, 2003.

SENSE AND HOLD CIRCUIT FOR HOSE ASSEMBLY

CROSS-REFERENCE TO RELATED APPLICATIONS

The present application claims priority to U.S. Provisional Patent Application No. 61/701,325, filed Sep. 14, 2012, and U.S. Provisional Patent Application No. 61/701,344, filed Sep. 14, 2012. The disclosures of each of those applications are hereby incorporated by reference in their entireties.

TECHNICAL FIELD

The present application relates generally to a hose assembly, and in particular to failure detection for a hose assembly. Specifically, the present application relates to a sense and hold circuit for a hose assembly.

BACKGROUND

High pressure reinforced hydraulic hose is typically used on a variety of fluid power operated machines, such as earth-moving machines, to provide a flexible connection between several moving parts of a hydraulic circuit employed on or within the machine. Such hoses may include a hollow polymeric inner tube on which successive cylindrical layers of reinforcing material, such as wire or textile, are concentrically applied to contain the radial and axial pressures developed within the inner tube.

Many applications are demanding hose constructions with both high burst strength and long term fatigue resistance. Using conventional technology, the burst strength of a hose design may be increased by adding additional reinforcing material and/or layers, a practice which is generally discouraged because of its negative impact on the flexibility of the hose, or by universally increasing the tensile strength of each layer of reinforcement material, which may come at the expense of hose fatigue resistance.

To determine the robustness of a hose design, a hose manufacturer typically performs, among other tests, an impulse test and a burst test on the hose. An impulse test measures a hose design's resistance to fatigue failure by cyclically subjecting the hose to hydraulic pressure. A burst test, on the other hand, is a destructive hydraulic test employed to determine the ultimate strength of a hose by uniformly increasing internal pressure until failure. Based on these and other tests, a manufacturer can estimate a hose life that can be used to determine when a hose has reached the end of its life and may require replacing.

In some circumstances, it is desirable to detect, in a non-destructive and non-disruptive manner a likelihood of failure of a hydraulic hose. One solution providing this capability is discussed in U.S. Pat. No. 7,555,936, and discloses connecting a monitor circuit between two parallel, at least partially-conductive layers of a hose wall. A change in an electrical property observed by that monitor circuit may indicate a change in a property of the hose wall structure that might indicate impending failure of the hose wall.

However, even with this solution, it can be difficult to determine whether the changed electrical property is in fact due to a change in a physical feature of a hose wall, or if the changed electrical property is due to a change in the sensing electronics, a change in an electrical property of a harness connecting the monitoring circuit to the hose wall, or simply degradation of an electrical connection to the hose wall. In these cases, there may be a change in an electrical property observed, even when hose wall integrity is not compromised.

For example, during normal use of such a hose, the hose and associated electrical connections thereto may become dirty or corroded by various environmental and use-case means. This corrosion effect should be monitored (and possibly compensated for) in order to ensure the best connection to and reading of the electrical characteristics of the hose.

Monitoring for electrical changes in a hose assembly can be difficult. This is because such electrical changes are likely to be, fleeting, at least during early failure events. For example, a pressure pulse occurring in a hydraulic hose can cause a momentary change of an electrical characteristic at the time of the pulse, but which reverts to a normal electrical characteristic after the pressure pulse event. If a monitoring circuit operates non-continuously, in that it does not provide constant monitoring of the electrical characteristic, it may be possible that the change in electrical characteristic occurring during the pulse is not detected.

For these and other reasons, improvements are desirable.

SUMMARY

In accordance with the following disclosure, the above and other issues are addressed by the following:

In a first aspect, a monitoring circuit configured to detect degradation of a hose assembly is disclosed. The monitoring circuit includes a voltage source connected to a first connection location of a hose assembly, the hose assembly including a hose having a first conductive layer and a second conductive layer, the first connection location electrically connected to the first conductive layer, wherein the second connection location is electrically connected to ground. The monitoring circuit also includes a capacitor electrically connected to the hose assembly via a differential voltage detection circuit, wherein a difference between a voltage at the voltage source and a voltage across the hose is captured by the capacitor. The monitoring circuit also includes a voltage sampling circuit configured to periodically detect a voltage at the capacitor, wherein, upon detecting a change in the voltage above a predetermined threshold, the voltage sampling circuit is configured to generate an alarm indicative of potential failure of the hose assembly.

In a second aspect, a method of monitoring a hose assembly is disclosed. The method includes applying a voltage to a first electrical connection of a hose assembly, the hose assembly including a hose having a first conductive layer and a second conductive layer, the first conductive layer electrically connected to the first connection location and the second conductive layer electrically connected to a second connection location that is connected to ground, and wherein the first and second conductive layers are separated by an insulating layer. The method also includes periodically monitoring a capacitor electrically connected at the first connection location by a differential voltage detection circuit, the capacitor forming a portion of a sense and hold circuit, and, upon detecting a voltage at the capacitor above a predetermined threshold, generating an alarm indicating a potential failure of the hose assembly.

In a third aspect, an integrated hose assembly having a monitoring system is disclosed. The integrated hose assembly includes a hose assembly having a first conductive layer electrically connected to a nipple and a second conductive layer electrically connected to a socket, the first and second conductive layers separated by an insulating layer, The integrated hose assembly also includes a monitoring circuit applied to the hose assembly and across the nipple and socket. The monitoring circuit includes a voltage source connected to a first connection location of a hose assembly, the hose assembly including a hose having a first conductive layer and a second conductive layer, the first connection location electrically connected to the first conductive layer, wherein the second connection location is electrically connected to ground. The monitoring circuit also includes a capacitor electrically connected to the hose assembly via a differential voltage detection circuit, wherein a difference between a voltage at the voltage source and a voltage across the hose is captured by the capacitor. The monitoring circuit also includes a voltage sampling circuit configured to periodically detect a voltage at the capacitor, wherein, upon detecting a change in the voltage above a predetermined threshold, the voltage sampling circuit is configured to generate an alarm indicative of potential failure of the hose assembly.

In a further aspect, a monitoring circuit includes a first pair of contacts electrically contacting a first connection location of a hose assembly, the first connection location electrically connected to a first conductive layer of the hose assembly. The monitoring circuit further includes a second pair of contacts electrically contacting a second connection location of a hose assembly, the second connection location electrically connected to a second conductive layer of the hose assembly separated from the first conductive layer of the hose assembly by an insulating layer. The monitoring circuit includes a circuit electrically connected to the first pair contacts and configured to obtain a first resistance between the first pair of contacts, wherein the circuit is electrically connected to the second pair contacts and configured to obtain a second resistance between the second pair of contacts. The monitoring circuit further includes a control circuit configured to compare the first and second resistances to a threshold value.

In a still further aspect, a method of compensating for contact resistances in a monitoring circuit for a hose assembly is disclosed. The method includes testing a resistance of contacts at an electrical connection location of a hose assembly, the resistance corresponding to a resistance across a pair of electrical contacts at the electrical connection location. The method also includes determining whether the resistance is greater than a threshold resistance, and upon determining that the resistance is below a threshold resistance, storing the resistance. The method further includes testing a resistance across a hose assembly, the hose assembly including a hose having a first conductive layer and a second conductive layer separated by an insulating layer, and wherein the first layer is electrically connected to the electrical connection location. The method includes determining the resistance across the hose assembly based at least in part by compensating for the resistance of contacts at the electrical connection location.

DETAILED DESCRIPTION

Figure 1:
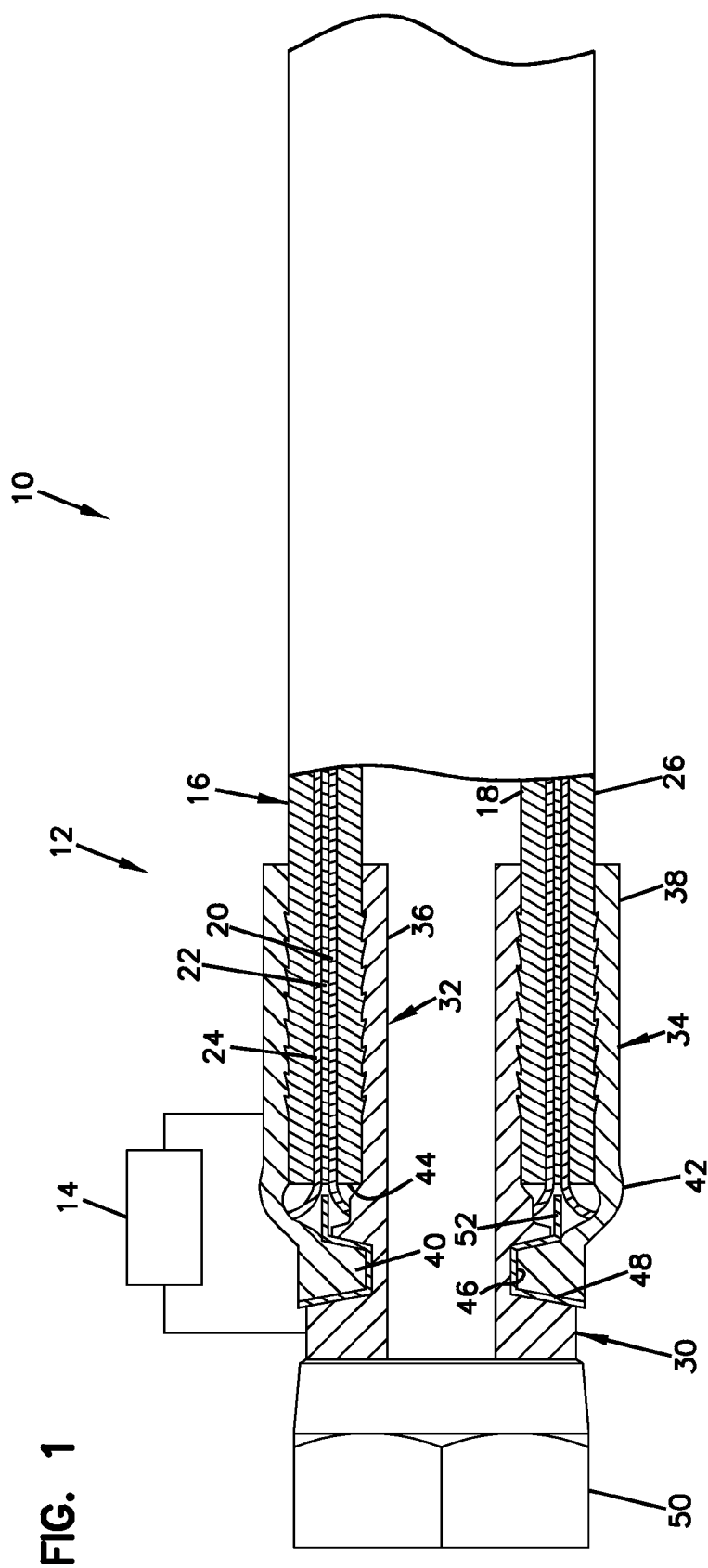
FIG. 1 is a partial cross-sectional view of an exemplary hose assembly employing a fault detector having exemplary features of aspects in accordance with the principles of the present disclosure.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In general the present disclosure relates to methods and systems for monitoring for potential degradation of a hose assembly as may occur in a hose assembly, and in particular transient changes to a hose assembly that may occur during pressure pulses experienced by a hydraulic hose. Generally, the methods and systems disclosed herein include capturing such transient occurrences by implementing a sense and hold circuit associated with the hose assembly, such that periodic checking of a held value can be performed to detect whether a transient failure event has occurred during a last sampling period.

Referring now to FIG. 1, an exemplary hose fault detection system 10 is shown in which such a monitoring arrangement can be implemented. The hose fault detection system 10 includes a hose assembly, generally designated 12, and a monitoring assembly 14 in electrical and physical communication with the hose assembly 12.

The hose assembly 12 includes a hose, generally designated 16, having a multi-layer construction. In the subject embodiment, the hose 16 is generally flexible and includes an inner tube 18 made from a polymeric material, such as rubber or plastic, or another material depending on the requirements of the particular application, a first conductive layer 20, an intermediate layer 22, a second conductive layer 24 and an outer cover 26. The first and second conductive layers 20, 24 define an electrical characteristic of the hose assembly 12, such as capacitance, inductance and/or resistance (impedance).

In the subject embodiment, the first conductive layer 20 overlays the inner tube 18 and the intermediate layer 22 overlays the first conductive layer 20. The second conductive layer 24 overlays the intermediate layer 22. The first and second conductive layers 20, 24 may be configured as reinforcing layers. The outer cover 26 may overlay the second conductive layer 24, and may include, for example, an extruded layer of rubber or plastic. The outer cover 26 may itself include a reinforcing layer.

The intermediate layer 22 operates to at least partially insulate electrically the first and second conductive layers 20, 24 from one another. The intermediate layer 22 may have any of a variety of constructions. For example, the intermediate layer 22 may consist of a single layer of an electrically resistive material. The intermediate layer 22 may also consist of multiple layers, wherein at least one of the layers exhibits electrical insulating properties. Certain composite materials may also be employed in the intermediate layer 22, such as a woven fabric bonded to a polymeric material. Composite materials having various other constructions may also be utilized. Composite materials may also be used in combination with other materials to form the intermediate layer 22.

The first and second conductive layers 20, 24 generally extend the entire length and span the entire circumference of the hose. This is generally the case when the conductive layer also functions as a reinforcement layer. The intermediate layer 22 may also extend over the entire length and circumference of the hose. There may be instances, however, where at least one of the first and second conductive layers 20, 24 extends only over a portion of the hose length and/or a portion of its circumference. In that instance, the intermediate layer 22 may also be configured to generally extend over the region of the hose containing the partial conductive layer 20, 24. The partial intermediate layer 22 may be positioned within the hose so as to separate the first and second conductive layers 20, 24 from one another.

Figure 2:
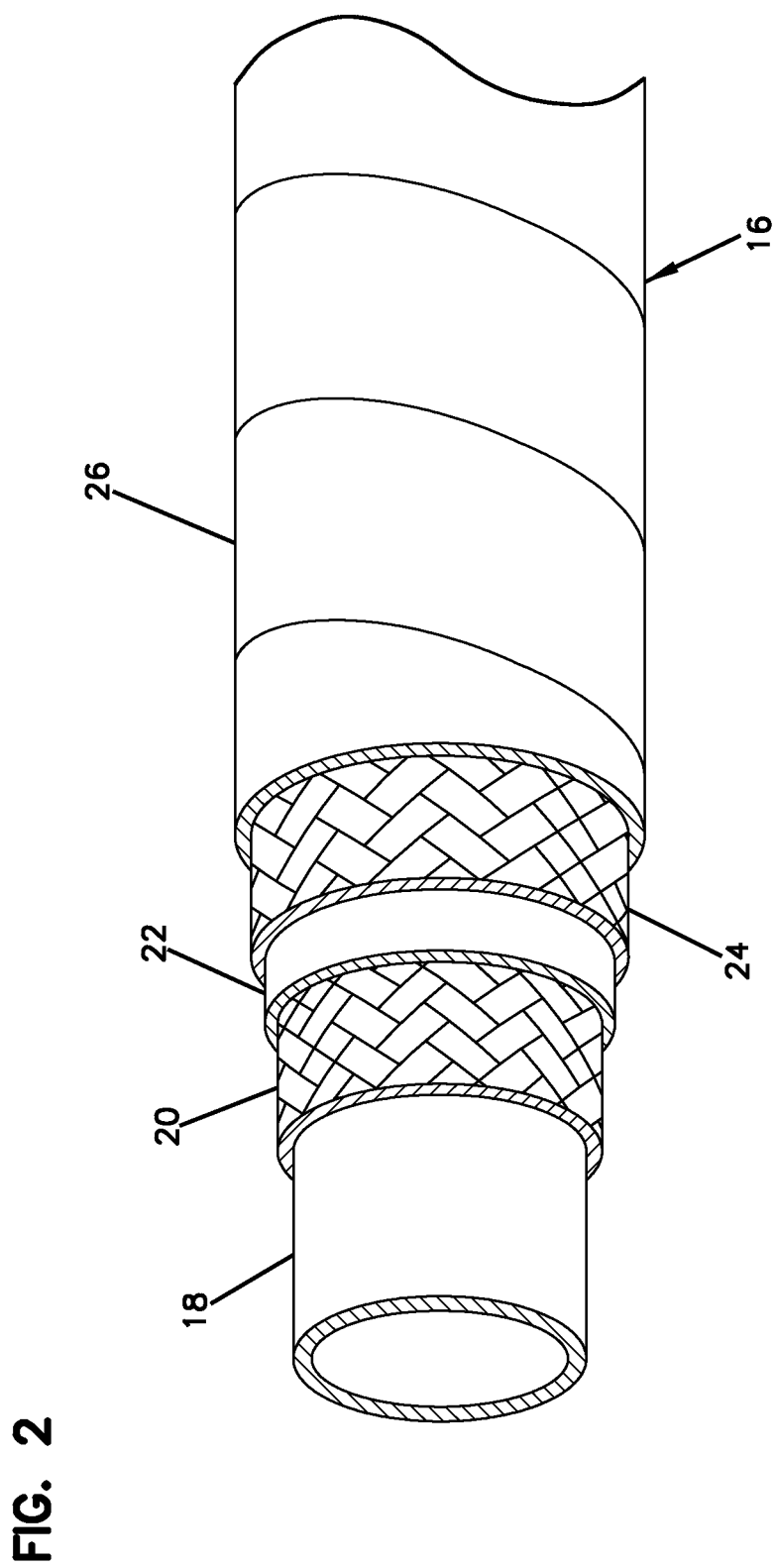
FIG. 2 is a perspective view, partially cut away, illustrating an exemplary hose employing a braided conductive layer that is suitable for use with the hose assembly of FIG. 1.
Figure 3:
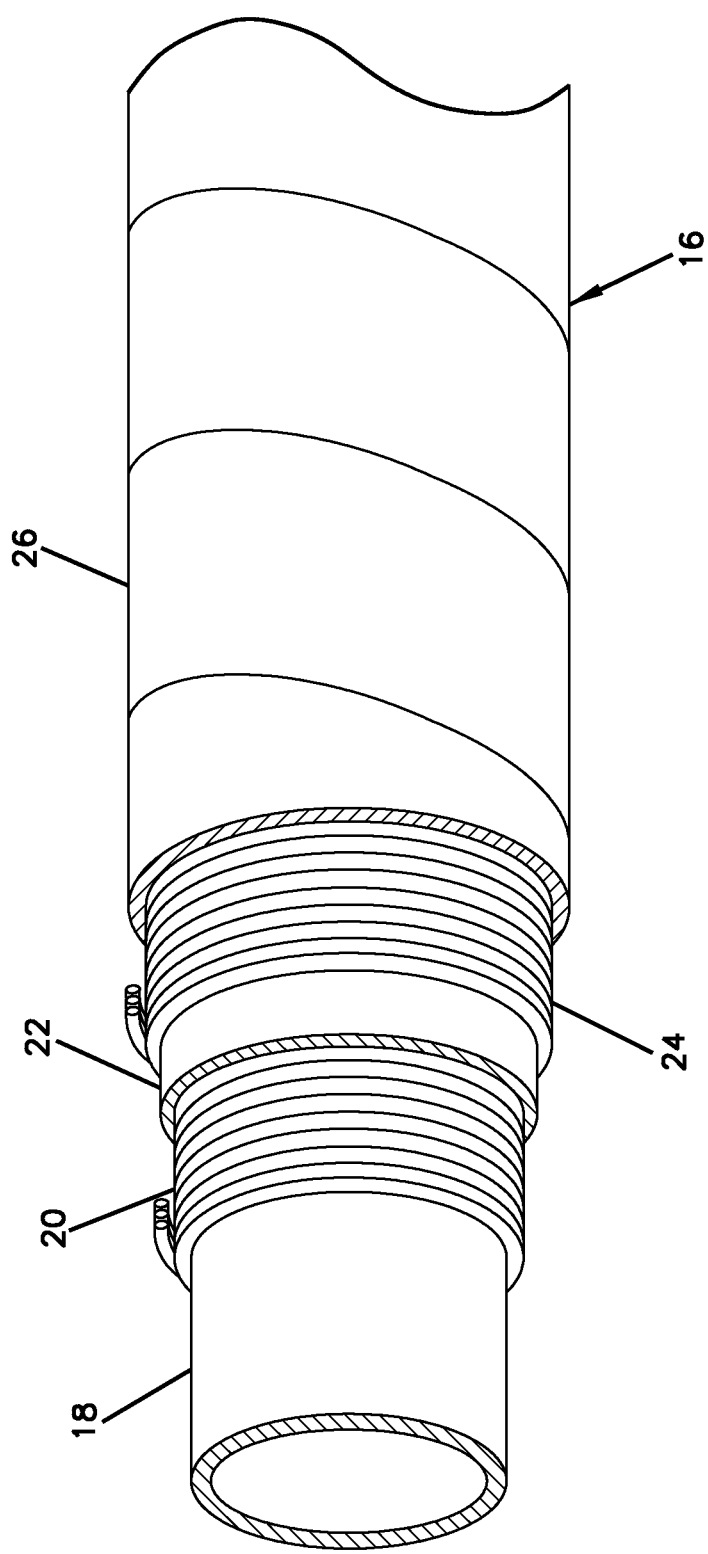
FIG. 3 is a perspective view, partially cut away, illustrating an exemplary hose employing a spiral wire conducting layer that is suitable for use with the hose assembly of FIG. 1.

Referring now to FIGS. 2 and 3, the first and second conductive layers 20, 24 may include, for example, an electrically conductive braided reinforcement material, such as shown in FIG. 2, or alternating layers of electrically conductive spiral reinforcement material, such as shown in FIG. 3. The braided reinforcement material may consist of a single layer or may include multiple layers. Although a two-wire spiral reinforcement arrangement is depicted in FIG. 3, it shall also be appreciated that other configurations, such as four and six wire arrangements, may also be utilized.

The first and second conductive layers 20, 24 may each have the same configuration, or each layer may be configured differently. For example, the first and second conductive layers 20, 24 may each include the braided material shown in FIG. 2, or one of the first and second conductive layers 20, 24 may include the braided material while the other of the first and second conductive layers 20, 24 may include the spiral reinforcement material shown in FIG. 3. Additionally, the first and second conductive layers 20, 24 may include a single ply or multiple plies of reinforcement material. The first and second conductive layers 20, 24 may comprise metal wire, natural or synthetic fibers and textiles, and other reinforcement materials, provided the selected material is electrically conductive. In general, when the hose assembly 12 is stressed, the layers 20, 24 can come into contact, either when a layer 22 completely degrades or in an instantaneous case where the layers momentarily connect.

Referring again to FIG. 1, the hose assembly 12 may include a hose fitting, generally designated 30, for fluidly coupling the hose 16 to another component. The hose fitting 30 may have any of a variety of different configurations depending, at least in part, on the requirements of the particular application.

In the subject embodiment, the hose fitting 30 includes a nipple, generally designated 32, that engages the inside of the hose 16 and a socket, generally designated 34, that engages the outside of the hose 16. The nipple 32 includes an elongated cylindrical end portion 36 that engages the inner tube 18 of the hose 16. A cylindrically shaped end portion 38 of the socket 34 engages the outer cover of the hose 16. The socket 34 and nipple 32 may be constructed from an electrically conductive material.

The socket 34 and nipple 32 can be secured to the hose 16 by crimping the end portion 38 of the socket 34 overlaying the hose 16. The crimping process deforms the end portion 38 of the socket 34, thereby compressing the hose 16 between the nipple 32 and the socket 34. In the subject embodiment, the portions of the nipple 32 and the socket 34 that engage the hose 16 include a series of serrations that at least partially embed into the relatively softer hose material when the socket 34 is crimped to help secure the hose fitting 30 to the hose 16. The serrations may be configured to prevent the serrations from penetrating the inner tube and outer cover and contacting the first and second conductive layers 20, 24.

In the subject embodiment, the socket 34 includes an inwardly extending circumferential lug 40 positioned near an end 42 of the socket 34 adjacent an end 44 of the hose 16. The lug 40 engages a corresponding circumferential slot 46 formed in the nipple 32 for securing the socket 34 to the nipple 32. The end 42 of the socket 34 having the lug 40 is initially formed larger than the nipple 32 to enable the socket 34 to be assembled onto the nipple 32. During the assembly process the end 42 of the socket 34 is crimped, which deforms the socket 34 and forces the lug 40 into engagement with the corresponding slot 46 in the nipple 32. The socket 34 can be electrically insulated from the nipple 32 by positioning an electrically insulating collar 48 between the socket 34 and nipple 32 at the point the lug 40 engages the slot 46.

The hose fitting 30 also includes a nut 50 rotatably attached to the nipple 32. The nut 50 provides a means for securing the hose assembly 12 to another component.

The first conductive layer 20 may be configured to extend beyond the end of the inner tube of the hose 16. The first conductive layer 20 may engage the nipple 32 to create an electrical connection between the nipple 32 and the first conductive layer 20. Similarly, the second conductive layer 24 may be configured to extend beyond an end of the outer cover of the hose 16. The second conductive layer 24 may engage the socket 34 to create an electrical connection between the socket 34 and the second conductive layer 24.

To help prevent the portions of the first and second conductive layers 20, 24 that extend beyond the end of the hose 16 from contacting one another, an electrically insulating spacer 52 may be positioned between the exposed ends of the first and second conductive layers 20, 24. The spacer 52 may be integrally formed as part of the collar 48 used to electrically insulate the socket 34 from the nipple 32. The spacer 52 may also be formed by extending the intermediate layer 22 of the hose 16 beyond an end of the inner tube 18 and outer cover 26. The spacer 52 may also be configured as a standalone component separate from the collar 48 and the intermediate layer 22 of the hose 16.

The monitoring assembly 14 may have any of a variety of configurations. In general, the monitoring assembly 14 is connectable over a portion of the hose assembly 12, in particular the portion illustrated in FIG. 1. The monitoring assembly 14, when installed over hose assembly 12, forms a physical and electrical connection with the hose assembly 12, and in particular to nipple 32 and socket 34, respectively. Generally, the monitoring assembly 14 detects an electrical characteristic of the hose assembly 12, while validating the connection to the nipple 32 and socket 34. An exemplary monitoring assembly 14 is described in further detail below, in connection with FIGS. 4-8.

Figure 4:
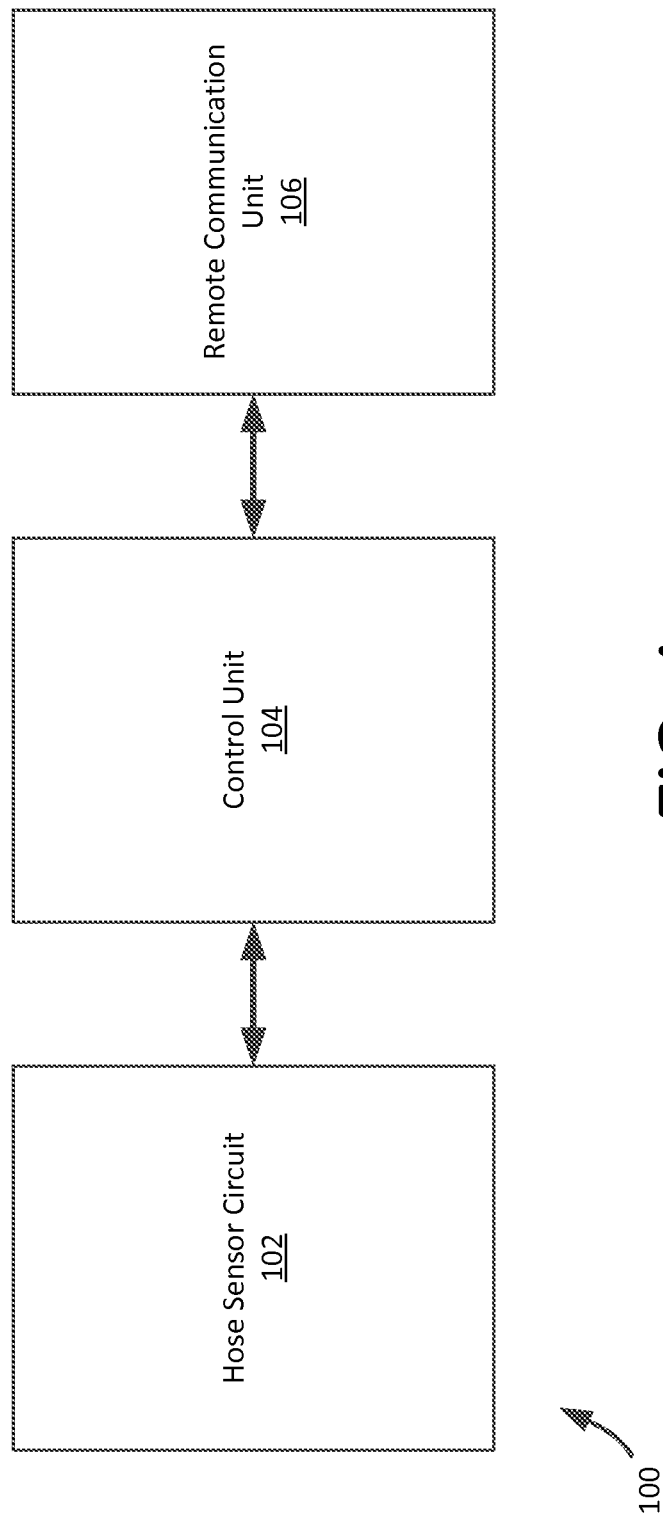
FIG. 4 is a block diagram of an example monitoring circuit used in connection with the hose assembly of FIG. 1.
Figure 5:
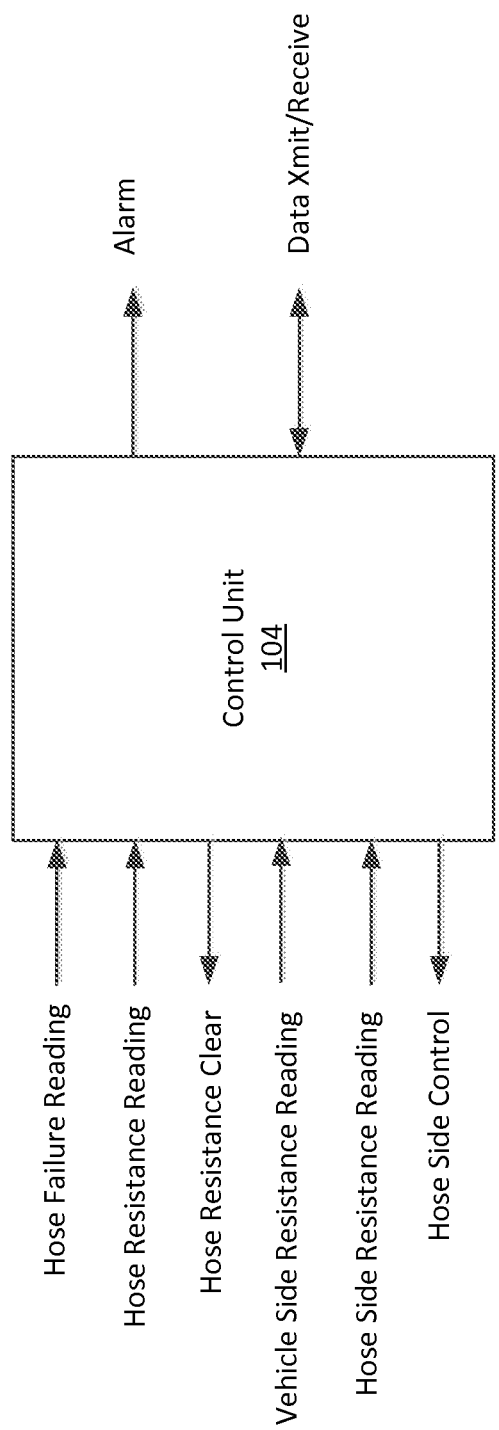
FIG. 5 is a block diagram of a controller useable in the monitoring circuit of FIG. 4.

Referring now to FIGS. 4-5, details regarding a monitoring circuit 100 are shown. The monitoring circuit 100 can be used within the monitoring assembly 14 to detect potential hose failures or hose degradation. The monitoring circuit 100 can be applied to the hose assembly 12 in any of a variety of manners; in some example embodiments, the monitoring circuit 100 is interconnected with the hose assembly 12 by a plurality of contacts having differing formats; example contact designs are illustrated in U.S. patent application Ser. No. 13/458,691, filed on Apr. 27, 2012, and entitled "Degradation Monitoring System for Hose Assembly", and U.S. Provisional Patent Application No. 61/701,307, filed Sep. 14, 2012, and titled "Wave Contact Arrangement for Hose Assembly", the disclosures of which are each incorporated by reference herein in their entireties. Of course, other contact arrangements could be used as well.

Figure 6:
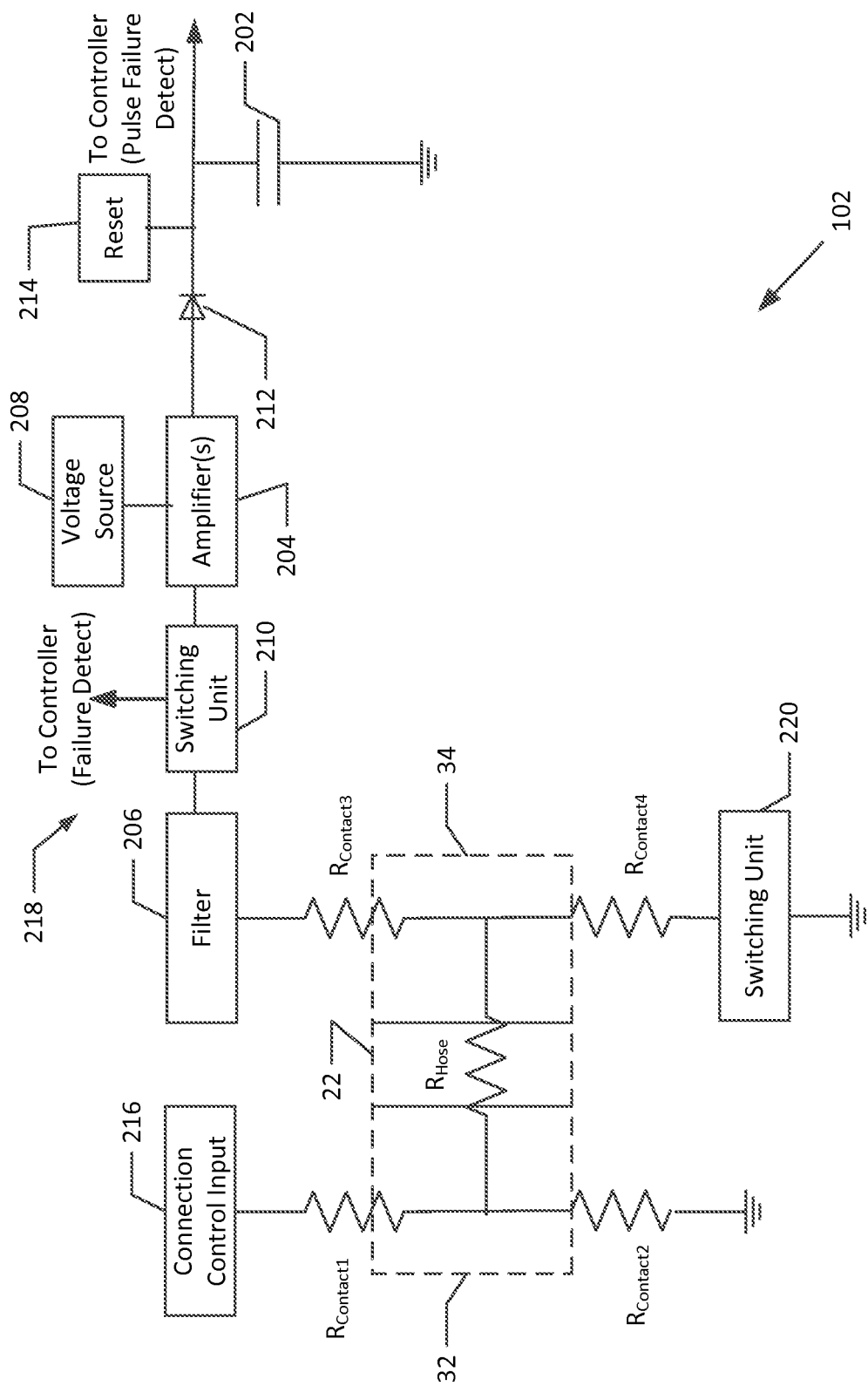
FIG. 6 is a schematic block diagram of an example hose interface circuit used within the monitoring circuit of FIG. 4.

Referring specifically to FIGS. 4-6, the monitoring circuit 100 includes a hose interface circuit 102 that is communicatively interfaced to a control circuit 104. The control circuit 104 is also communicatively connected to a communication circuit 106.

In general, the hose interface circuit 102 provides, based on control signals from the control circuit 104, a voltage across contacts to the nipple and socket of the hose assembly 12, as illustrated above via the monitoring assembly 14. Based on a sensed resistance of the hose assembly, the current state of that hose assembly can be detected. In general, a higher resistance indicates that the insulating layer 22 between conductive layers 20, 24 has not weakened or degraded, and as such it can be assumed that the hose wall remains in adequate operational condition. One example of such a hose interface circuit is illustrated in FIG. 6, below.

The control circuit 104 generally provides voltage control to the hose interface circuit 102, and periodically monitors the resistance of a circuit including the hose assembly 12 to detect, over time, changes in the resistance of the hose assembly 12. In general, once the resistance of the hose assembly drops below a predetermined threshold, it can be assumed that the hose assembly has been compromised, indicating contact or near-contact between layers 20, 24 due to a temporary or persistent failure of the insulating layer 102. The control circuit 104 can also generate alarms and otherwise provide communication with remote systems via the communication circuit 106.

In specific reference to FIG. 5, the control circuit includes hose failure reading, hose resistance reading, and both vehicle and hose side resistance reading inputs, as well as a hose resistance clearance and hose side control outputs, operation of which are discussed in further detail below.

The communication circuit 106 is configured to communicate status of the hose assembly 12, as detected using the hose interface circuit 102 and the control circuit 104, to remote locations. In various embodiments, the communication circuit 106 can be a wired or wireless communication unit. As illustrated in FIG. 5, the control circuit 104 provides a bidirectional data communication interface to the communication circuit 106, and optionally provides an alarm signal to generate either a local alarm or to pass the alarm to the communication unit for communication to a remote system.

Referring now to FIG. 6, a hose interface circuit 102 is shown. In the hose interface circuit 102, a form of sense and hold circuit is implemented to detect impulse-based changes in a resistance value (or other changes occurring between samplings of the resistance value) of the hose assembly 12.

As seen in FIG. 6, the hose assembly is depicted schematically, with separate nipple 32 and socket 34 connections separated by insulating layer 22. The hose has a resistance, noted as $R_{hose}$, that is experienced generally across the insulating layer. During normal operation of the hose assembly, the insulating layer provides a high resistance, generally in the range of 100 kOhms or more. In addition, the monitoring assembly 14 has contacts to the hose, which have a resistance at the point of contact with the hose. Generally, the monitoring assembly has a pair of contacts at each of the nipple ($R_{contact1}$, $R_{contact2}$) and socket ($R_{contact3}$, $R_{contact4}$), respectively.

In the embodiment shown, the hose interface circuit 102 includes a capacitor 202 connected to ground. The capacitor 202 is configured to receive and hold a voltage level from an amplifier arrangement 204. The amplifier arrangement 204 includes a differential amplifier and optionally one or more scaling amplifiers. The amplifier arrangement 204 has as an input a voltage drop across the hose assembly 12, as received through a filter circuit 206. The amplifier arrangement compares that voltage to a known constant voltage, which is derived from a voltage source 208. To the extent these voltages differ, a signal appears on the amplifier output, and is passed to the capacitor 202. In some embodiments, the voltage source 208 can be a battery-operated voltage source; in other embodiments, a wired dc voltage is provided.

In further detail regarding the operation of circuit 102, the voltage source 208 will be applied, through a switching unit 210 and filter circuit 206 across the hose assembly 12 to ground (e.g., through $R_{contact3}$ and $R_{contact2}$. As such, a voltage drop will be experienced across the hose assembly that is particularly attributable to $R_{hose}$. This voltage drop will be the majority of the voltage level of the voltage source 204, despite other resistances in the circuit (e.g., within the amplifier arrangement 204). In this steady "normal" state, the capacitor 202 will generally receive a low voltage level due to the small difference between the expected voltage (derived by a voltage divider connected to voltage source 208) and the actual voltage drop across the hose assembly 12. Output of the amplifier arrangement 204 is captured at the capacitor 202 due to placement of a diode 212 between the amplifier arrangement 204 and the capacitor 202, preventing the capacitor from discharging back to a steady state operation in the event that the lowered $R_{hose}$ condition (and therefore high signal generated by a differential amplifier within the amplifier arrangement 204) was transient (non-persistent).

The switching unit 210 allows for selective switching between monitoring of a continuously variable electrical property of the hose assembly and a captured peak value of the electrical characteristic between sampling events. In some embodiments, the electrical characteristics of the hose can be monitored, such as to detect contact resistances or other fault signatures/characteristics by performing periodic current-time readings of electrical characteristics.

Relating specifically to the sense-and-hold functionality described herein, in the event of a faulty hose, the $R_{hose}$ value can drop significantly, for example from about 100 kOhms to less than about 200 Ohms. Using the sense and hold circuitry illustrated herein, and in particularly the capacitor 202 and amplifier arrangement 204, if the hose becomes faulty for an instant, (i.e., $R_{hose}$ drops during a high pressure pulse event through the hose, indicating a weakening of the hose), the voltage at the capacitor 202 will generally rise due to the difference between the hose voltage drop and the constant voltage from the voltage divider of the amplifier arrangement, but the capacitor voltage will not fall even if the $R_{hose}$ level returns to a high resistance (due to diode 212). In this way, the capacitor 202 captures and holds a peak voltage that represents a lowest resistance value for Rhose during a given period of time (e.g., between sampling events). A connection to the control circuit (shown as off-page reference connected to capacitor 202) allows the control circuit to periodically sample the voltage level of the capacitor 202 to determine if the voltage level at the capacitor is sufficiently high to indicate that a low-resistance event occurred on the hose assembly 12. After sampling the capacitor value, the control circuit 104 of FIG. 6 can reset the capacitor value using a reset circuit 214, which allows the capacitor to drain to a low voltage level, for continued monitoring of the hose resistance. Additional details regarding operation of the sense and hold circuitry are discussed below in connection with FIG. 7

It is noted that the circuit 102 includes a number of other switching functions as well, which allow diagnostic testing of the hose and hose contacts. In the embodiment shown, voltage regulation and detection circuits 216, 218, respectively, are electrically connected to the nipple 32 and socket 34, respectively, connected to $R_{contact1}$ and $R_{contact3}$. In addition, a switching unit 220 can be positioned between $R_{contact4}$ and ground. The switching unit 220 selectively allows connection of $R_{contact4}$ to ground, for example in the case where contact resistances are to be tested. In normal operation in which $R_{hose}$ is monitored, $R_{contact4}$ remains electrically isolated from ground, to ensure that electrical connection is made across $R_{hose}$.

In general, in another aspect discussed in further detail below in connection with FIG. 8, the circuit 102 can operate in a different mode to detect corrosion of electrical contacts to the hose assembly 12, or other electrical disconnection from the hose (e.g., due to loss of contact). In this arrangement, contact resistances $R_{contact1}$-$R_{contact4}$ are tested, with voltages applied across a circuit including $R_{contact1}$ and $R_{contact2}$ at the nipple, and then across $R_{contact3}$ $R_{contact4}$ at the socket. Based on the detected resistances, this contact resistance can either be stored by the control circuit and accommodated for during monitoring of $R_{hose}$, or to the extent the contact resistance is sufficiently high to indicate a connectivity issue regarding the hose contacts, an alarm can be generated.

In addition, as discussed above, switching unit 210 allows for selection between a current value of an electrical characteristic and the peak captured value of the electrical characteristic at the capacitor 202.

Figure 7:
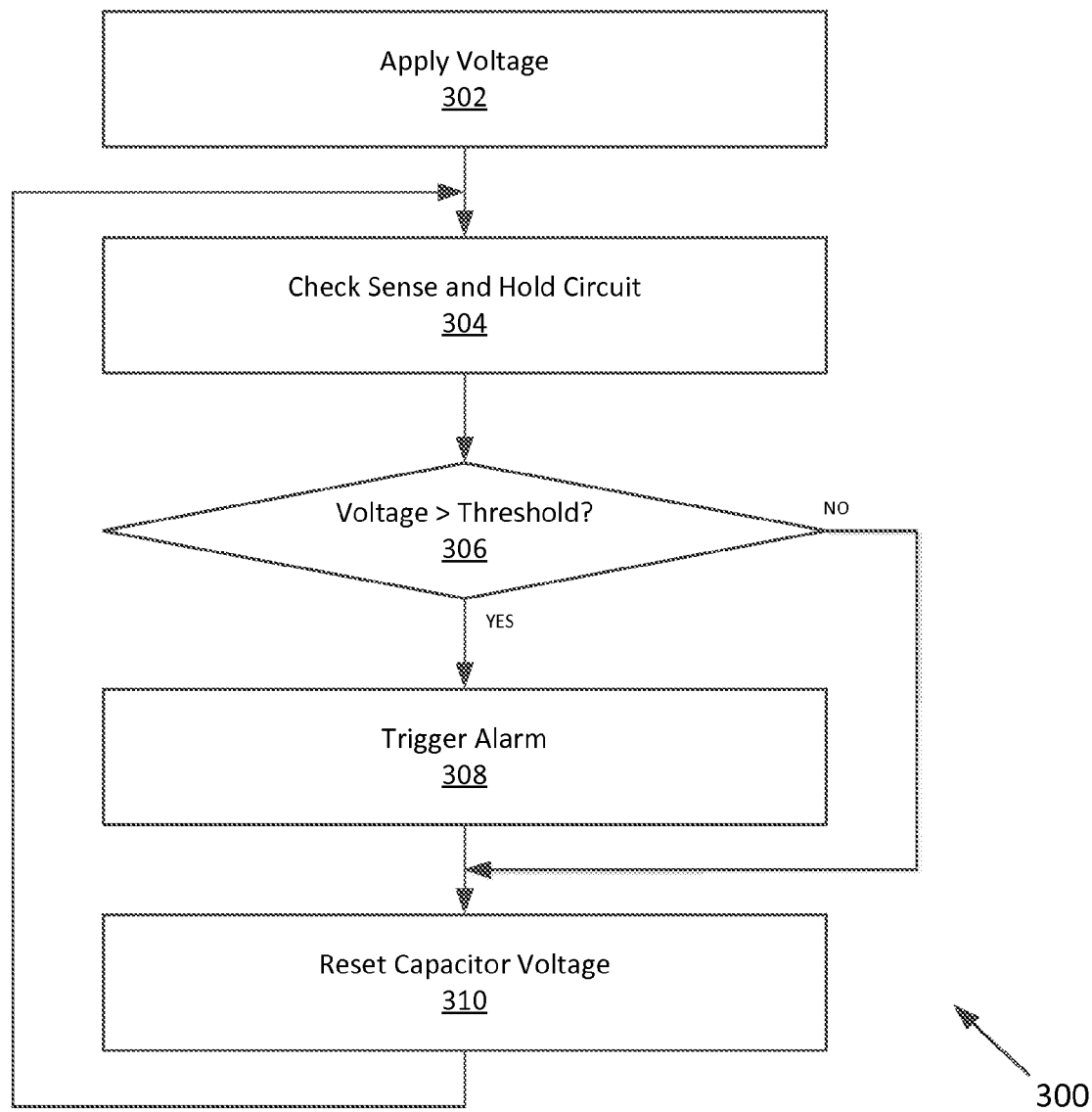
FIG. 7 is a flowchart of a method for monitoring potential hose assembly degradation via a sense-and-hold arrangement, according to a possible embodiment.

FIG. 7 is a flowchart of a method 300 for monitoring potential hose assembly degradation via a sense-and-hold arrangement, according to a possible embodiment of the present disclosure. The method 300 can be performed, for example, by the control circuit 104 as interfaced to the hose interface circuit 102. The method 300, in various embodiments, can be implemented in hardware or software, for example as a sequence of computer implemented steps, operations, or procedures running on a programmable circuit.

In general the method 300 begins by applying a continuous voltage across a hose assembly 102 (step 302). The method continues when, at some predetermined time or period of time, a control circuit checks a voltage level captured on a sense and hold circuit, such as on capacitor 202 (step 304). The control circuit 104 can then determine if a voltage maintained on the sense and hold circuit is greater than a threshold voltage, indicating that a fault (or other event where $R_{hose}$ was a low value) occurred at some time prior to the sampling of the voltage level by the control circuit (step 306). If the voltage is greater than a threshold voltage level (indicating that $R_{hose}$ was below a threshold resistance), the control circuit 104 can trigger an alarm (step 308). Regardless of whether the threshold voltage was exceeded, the control circuit 104 can then activate a reset circuit, discharging the sense and hold circuit (i.e., discharging capacitor 202), to essentially restart the process (step 310).

The control circuit 104 can opt to sample the sense and hold circuit at any desired frequency, depending upon the power consumed by the control circuit, battery capacity (if applicable), and the resolution at which fault events are desired to be detected.

Figure 8:
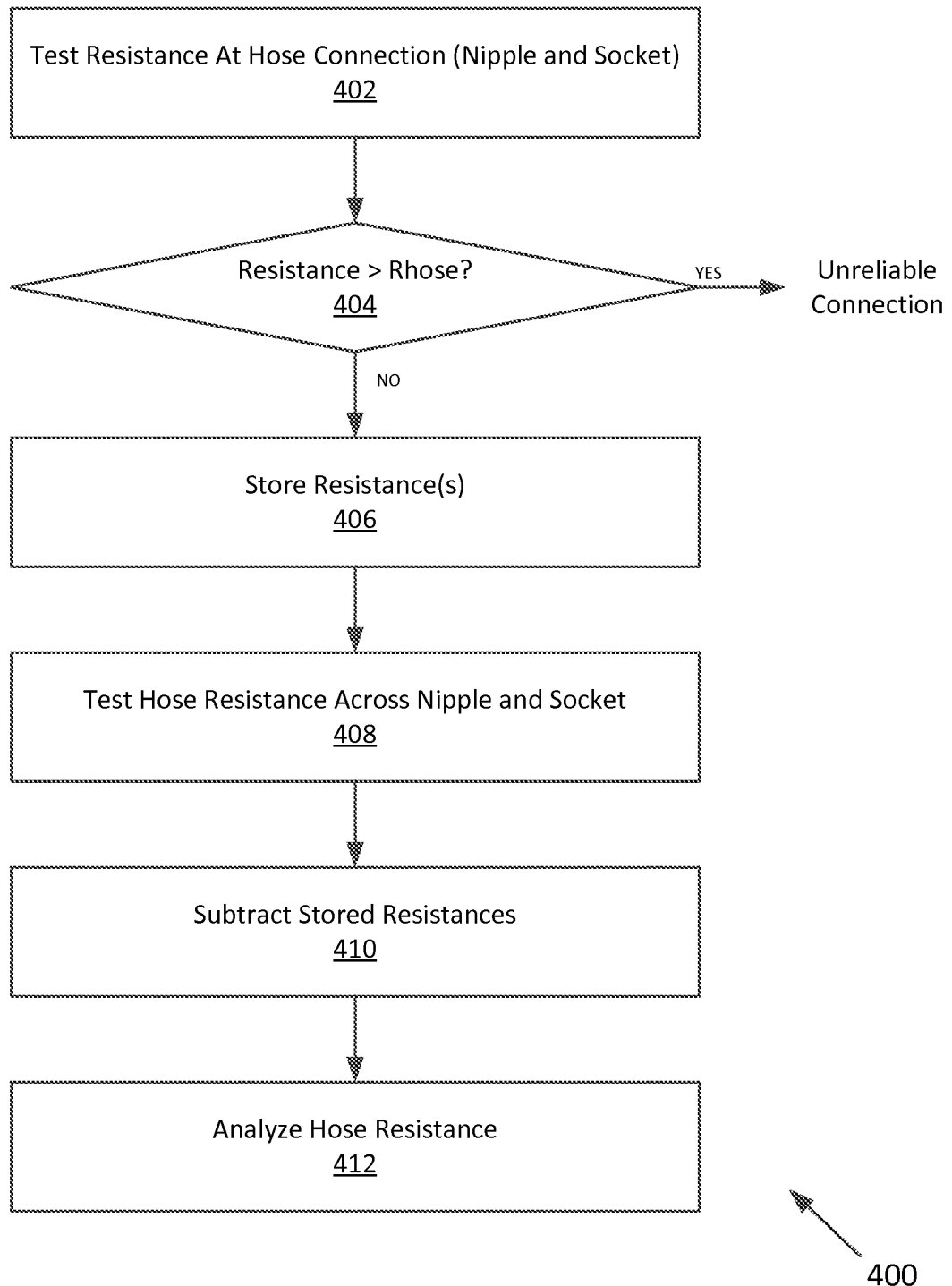
FIG. 8 is a flowchart of a method for monitoring and accounting for contact resistance using the hose interface circuit of FIG. 6.

FIG. 8 is a flowchart of a method 400 for monitoring and accounting for contact resistance using the hose interface circuit of FIG. 6. In general the method 400 provides for side resistance accommodation, and to ensure that an accurate $R_{hose}$ reading can be accomplished without interference by resistance due to the circuit contacts interfaced to the hose. The method 400, in various embodiments, can also be implemented in hardware or software, for example as a sequence of computer implemented steps, operations, or procedures running on a programmable circuit.

The method 400 is initiated by setting a side resistance value, for example by activating such a signal from the control circuit 104. Setting the side resistance value causes switching unit 220 of FIG. 6 to allow voltages to be provided across the circuit contacts, in particular across contacts $R_{contact1}$ and $R_{contact2}$ and then separately across $R_{contact3}$ and $R_{contact4}$ (step 402). These resistances are compared to a predetermined threshold value (step 404), above which it is assumed that at least one of the contacts has lost connection to the nipple or socket, respectively. Because these resistances in theory should be approximately zero Ohms, in some embodiments, the threshold value is about 50 Ohms to provide for some resistance allowed but quickly indicating potential connectivity issue. However, other resistances could be used as well. If the resistance is above the preset threshold, the control circuit 104 generates an alarm and/or message indicating that the resistance is too high, indicating a possible faulty connection to the hose.

If the aggregate resistances across the nipple and socket connections do not exceed the threshold resistance, rather than alarming, the control circuit 104 accommodates those resistances by storing those resistances (step 406) and when testing a hose resistance (step 408), subtracting these measured contact resistances from that value (step 410). This adjusted hose resistance can then be used as a more accurate hose resistance, for example for purposes of determining the point at which hose degradation and/or failures occur.

Referring now to the application generally, it is noted that the sense and hold circuitry of the present disclosure provides a number of advantages, in particularly in the context of a battery-powered system used for a monitoring circuit. Due to power conservation and battery capacity limitations, it is desirable for a controller or other control circuit to operate at a low frequency, sampling or monitoring the hose assembly every few minutes or hours, rather than continuously. As such, by capturing transient events in the circuitry interfaced to the hose, the controller can simply wait and detect any such events indicating the presence of a fault at a low frequency, but without missing such events.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A monitoring circuit configured to detect degradation of a hose assembly, the circuit comprising:
a voltage source connected to a first connection location of a hose assembly, the hose assembly including a hose having a first conductive layer and a second conductive layer, the first connection location electrically connected to the first conductive layer, wherein the second connection location is electrically connected to ground;
a capacitor electrically connected to the hose assembly via a differential voltage detection circuit, wherein a difference between a voltage at the voltage source and a voltage across the hose is captured by the capacitor;
a voltage sampling circuit configured to periodically detect a voltage at the capacitor, wherein, upon detecting a change in the voltage above a predetermined threshold, the voltage sampling circuit is configured to generate an alarm indicative of potential failure of the hose assembly.

2. The circuit of claim 1, further comprising a differential amplifier electrically connected between the first connection location and the capacitor, the differential amplifier configured to scale the voltage differences on the capacitor based on changes in the resistance.

3. The circuit of claim 2, wherein the differential amplifier is configured to, in the event of a short duration lowering of the resistance of the hose assembly, provide a voltage to the capacitor such that the capacitor retains additional voltage thereon.

4. The circuit of claim 2, further comprising a diode connected between an output of the differential amplifier and the capacitor.

5. The circuit of claim 1, wherein the voltage sampling circuit is configured to, upon detection that the voltage is above the predetermined threshold, clear the additional voltage from the capacitor.

6. The circuit of claim 5, wherein the voltage sampling circuit is configured to clear the additional voltage from the capacitor after generating the alarm.

7. The circuit of claim 1, wherein the resistance comprises a resistance value during an event experienced by the hose.

8. The circuit of claim 7, wherein the event comprises an impulse event occurring at a time different from a time at which the voltage sampling circuit periodically detects voltage at the capacitor.

9. The circuit of claim 1, wherein the voltage sampling circuit comprises a microcontroller.

10. The circuit of claim 1, further comprising a communication circuit communicatively connected to the voltage sampling circuit and configured to, upon receiving a signal from the voltage sampling circuit regarding the alarm, communicate the alarm remotely from the hose assembly.

11. The circuit of claim 10, wherein the communication circuit comprises a wireless communication interface.

12. The circuit of claim 1, wherein the first connection location comprises a nipple of the hose assembly and the second connection location comprises a socket of the hose assembly.

13. A method of monitoring a hose assembly, the method comprising:
applying a voltage to a first electrical connection of a hose assembly, the hose assembly including a hose having a first conductive layer and a second conductive layer, the first conductive layer electrically connected to the first connection location and the second conductive layer electrically connected to a second connection location that is connected to ground, and wherein the first and second conductive layers are separated by an insulating layer;
periodically monitoring a capacitor electrically connected at the first connection location by a differential voltage detection circuit, the capacitor forming a portion of a sense and hold circuit;
upon detecting a voltage at the capacitor above a predetermined threshold, generating an alarm indicating a potential failure of the hose assembly.

14. The method of claim 13, further comprising communicating the alarm to a location remote from the hose assembly.

15. The method of claim 13, further comprising clearing the voltage at the capacitor to a level below the predetermined threshold.

16. The method of claim 13, wherein applying the voltage comprises applying a continuous voltage.

17. The method of claim 13, wherein the first connection location is at a nipple and the second connection location is at a socket.

18. An integrated hose assembly having a monitoring system, the integrated hose assembly comprising:
a hose assembly having a first conductive layer electrically connected to a nipple and a second conductive layer electrically connected to a socket, the first and second conductive layers separated by an insulating layer;
a monitoring circuit applied to the hose assembly and across the nipple and socket, the monitoring circuit including:
a voltage source connected to a first connection location of a hose assembly, the hose assembly including a hose having a first conductive layer and a second conductive layer, the first connection location electrically connected to the first conductive layer, wherein the second connection location is electrically connected to ground;
a capacitor electrically connected to the hose assembly via a differential voltage detection circuit, wherein a difference between a voltage at the voltage source and a voltage across the hose is captured by the capacitor;
a voltage sampling circuit configured to periodically detect a voltage at the capacitor, wherein, upon detecting a change in the voltage above a predetermined threshold, the voltage sampling circuit is configured to generate an alarm indicative of potential failure of the hose assembly.

19. The integrated hose assembly of claim 18, wherein the voltage source is applied continuously across a circuit including connections to the nipple and socket.

20. The integrated hose assembly of claim 18, wherein the differential voltage detection circuit comprises a differential amplifier.

21. The integrated hose assembly of claim 18, wherein the monitoring circuit further includes:
a first pair of contacts electrically contacting the first connection location of a hose assembly;
a second pair of contacts electrically contacting the second connection location of a hose assembly;
a circuit electrically connected to the first pair contacts and configured to obtain a first resistance between the first pair of contacts;
wherein the circuit is electrically connected to the second pair contacts and configured to obtain a second resistance between the second pair of contacts; and wherein the voltage sampling circuit includes a control circuit configured to compare the first and second resistances to a threshold value.

22. The monitoring circuit of claim 21, wherein the control circuit is further configured to, upon detecting that the first or second resistances exceed the threshold value, generate an alarm.

23. The monitoring circuit of claim 21, wherein the control circuit is further configured to detect a resistance between the first connection location and the second connection location by detecting an overall resistance at the circuit and at least partially compensating for the first and second resistances.

* * * * *